United States Patent
Dobler et al.

(10) Patent No.: US 9,623,136 B2
(45) Date of Patent: Apr. 18, 2017

(54) AUTO AIR FRESHENER

(71) Applicants: Sven Dobler, Huntington, NY (US); Dale Beal, Augusta, GA (US)

(72) Inventors: Sven Dobler, Huntington, NY (US); Dale Beal, Augusta, GA (US)

(73) Assignee: Orlandi, Inc., Farmingdale, NY (US)

( * ) Notice: Subject to any disclaimer, the term of this patent is extended or adjusted under 35 U.S.C. 154(b) by 740 days.

(21) Appl. No.: 13/694,066

(22) Filed: Oct. 25, 2012

(65) Prior Publication Data

US 2013/0056549 A1 Mar. 7, 2013

Related U.S. Application Data

(63) Continuation of application No. 12/657,743, filed on Jan. 26, 2010, now abandoned.

(60) Provisional application No. 61/207,009, filed on Feb. 6, 2009.

(51) Int. Cl.
*A61L 9/12* (2006.01)
*A61L 9/04* (2006.01)

(52) U.S. Cl.
CPC . *A61L 9/12* (2013.01); *A61L 9/04* (2013.01); *A61L 2209/12* (2013.01); *A61L 2209/15* (2013.01)

(58) Field of Classification Search
CPC .......... A61L 9/12; A61L 9/04; A61L 2209/12; A61L 2209/15
USPC .............................................. 239/53, 57, 60
See application file for complete search history.

(56) References Cited

U.S. PATENT DOCUMENTS

| | | | |
|---|---|---|---|
| 1,744,560 A | 1/1930 | Lukacs | |
| 2,757,957 A * | 8/1956 | Samann | 239/53 |
| 3,065,915 A | 11/1962 | Samann | |
| 4,824,707 A | 4/1989 | Spector | |
| 4,883,692 A | 11/1989 | Spector | |
| 4,920,675 A * | 5/1990 | Mashimo | 40/492 |
| 5,148,983 A * | 9/1992 | Muniz | 239/56 |
| 5,334,361 A * | 8/1994 | Rafaelides et al. | 422/305 |
| 5,529,243 A | 6/1996 | Hoyt et al. | |
| 5,823,432 A * | 10/1998 | Hogan | 239/36 |
| D453,374 S | 2/2002 | Taylor | |
| 6,367,184 B1 | 4/2002 | Kheder | |
| 6,625,914 B1 * | 9/2003 | Sud | 40/743 |
| 7,926,735 B1 * | 4/2011 | Mobley | 239/53 |
| 2008/0099576 A1 | 5/2008 | Hart | |

* cited by examiner

*Primary Examiner* — Arthur O Hall
*Assistant Examiner* — Chee-Chong Lee
(74) *Attorney, Agent, or Firm* — Paul M. Denk

(57) ABSTRACT

An auto air freshener provides a parallel spaced apart board and a card that suspending from a hang point. The auto air freshener has a blotter board that includes fragrance oil and other enhancers, a facer card having printed graphics upon one or both surfaces, a clip that spaces the board and the card apart, and a flexible elongated loop that hangs the freshener at a location selected by the user. Alternatively, a pedestal supports the board and the card upright. The freshener invention separates the delivery of fragrance from the visual display of graphics. The separation allows for the manufacture and the usage of the blotter board and the facer card with improved print quality and wider selection of fragrances.

4 Claims, 4 Drawing Sheets

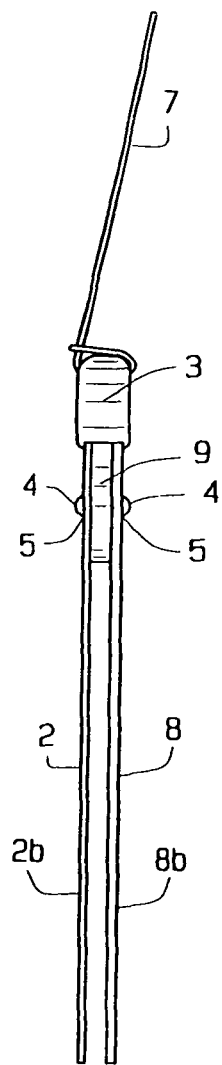
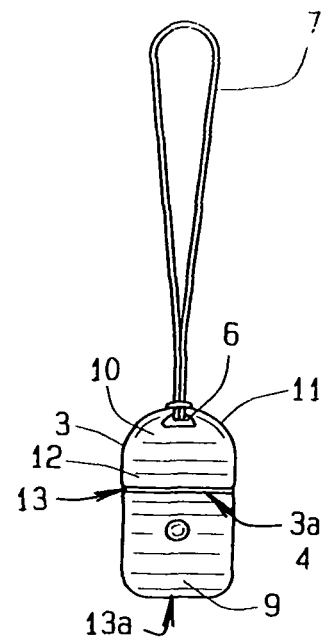
FIG.4
FIG.3
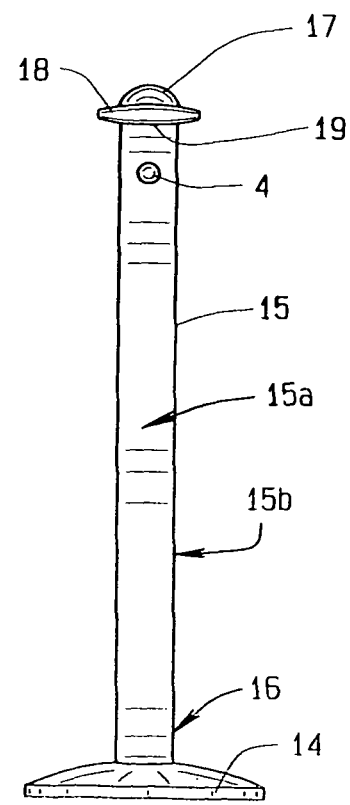
FIG.5

AUTO AIR FRESHENER

CROSS REFERENCE TO RELATED APPLICATION

This continuation patent application claims priority to the non-provisional patent application having Ser. No. 12/657,743, having filing date Jan. 26, 2010, which claims priority to the provisional patent application having Ser. No. 61/207,009, having filing date Feb. 6, 2009.

BACKGROUND OF THE INVENTION

The framed freshener generally relates to air freshening devices and more specifically to a blotter freshener separated from a printed card.

Over the years as automobiles and trucks developed, the passenger cabins and truck cabs became more and more sealed. To improve driver comfort, cabins and cabs became heated and cooled by various systems. Then as oil prices rose, heating and cooling systems faced pressure to become more efficient and lessen demand upon engines and power sources. Efficient heating and cooling systems called for tighter sealing of cabins and cabs. To improve driver comfort and safety, cabins and cabs became sealed at the doors against water and fume intrusion. Driver preference for a quiet ride with a minimum of road noise led to tighter sealing of cabins and cabs. Well sealed cabins and cabs make for a comfortable and safe ride for drivers. However, odors and fumes within a cabin and cab tend to linger because of the seals.

Companies have developed various fresheners to mask odors and fumes within a cabin of a car and the cab of a truck. The fresheners generally hang from a rear view mirror or other suitable anchoring point. The fresheners then release a fragrance over time to make the driver's environment more pleasant. The fresheners can be plain or have printing upon them for various marketing and advertising purposes.

DESCRIPTION OF THE PRIOR ART

Fresheners come from various materials. The popular fresheners for the automotive market include the blotter type. The blotter has a rigid paperboard impregnated with a fragrance. Drivers have utilized the blotter freshener in great numbers due to its low cost and ease of use. The blotter accepts printing upon its surfaces and can be made in various shapes, including prevalent imitation conifer trees. The paperboard of the blotter retains its surface characteristics, such as texture and roughness.

These characteristics inhibit the quality of printing upon blotters. The rough texture of blotter absorbs much fragrance but accepts few fine details of printing. Existing blotter fresheners often have single words, phrases, or logos printed upon them but not multiple colors or camera ready artwork.

Automotive air fresheners also include a variety of gel products. The gel products attract drivers due to their softness, color, and introduction of a scent or is fragrance. The gel fresheners, by their material properties, spark consumer demand. The gel fresheners contain a high percentage of mineral oil and attain various shapes. Additionally, the careful selection of the composition of gel products has related the good dispersion between a scent or fragrance and the surface of the gel products for introduction into the atmosphere. Gel fresheners retain printing upon their surface however, the printing generally has one color, limited numbers of words, and crude detail in logos.

The present invention overcomes the disadvantages of the prior art and provides automotive air freshener that disperses a fragrance while allows detail printed decoration of the freshener. The automotive air freshener has fragrance embedded upon one planar member and detailed printed decoration upon a parallel planar member. The invention freshens the cabins and cabs of vehicles while providing more detailed printed images for drivers and others to view.

SUMMARY OF THE INVENTION

Generally, the present invention of an auto air freshener provides a parallel spaced apart board and a card that suspending from a hang point. The auto air freshener has a blotter board that includes fragrance oil and other enhancers, a facer card having printed graphics upon one or both surfaces, a clip that spaces the board and the card apart, and a flexible elongated loop that hangs the freshener at a location selected by the user. The freshener invention separates the delivery of fragrance from the visual display of graphics allowing for manufacture and usage of the blotter board and the facer card with improved print quality and broadens selection of fragrances.

There has thus been outlined, rather broadly, the more important features of the invention in order that the detailed description thereof that follows may be better understood and that the present contribution to the art may be better appreciated. The present invention also includes a clip that mechanically engages the blotter board and facer card yet still spaces them apart, a frame that separates the blotter board and facer card, a pedestal mount, an additional facer card wherein the fragrance card occupies the center of a three card and board arrangement, and a surface texture upon the blotter board including debossing that slows release of fragrance therefrom. Additional features of the invention will be described hereinafter and which will form the subject matter of the claims attached.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

One object of the present invention is to provide an auto air freshener with higher quality and more detailed printing in relation to a fragrant blotter card.

Another object is to provide such an auto air freshener with separated components that improves the inventory control and logistics management during manufacturing and later during sales.

Another object is to provide such an auto air freshener that separates the visual function of the invention from its delivery of fragrance.

Another object is to provide such an auto air freshener that improves the aesthetics for the consumer and increases the flexibility of marketers and manufacturers.

Another object is to provide such an auto air freshener that separates the graphic elements from the blotter board.

Another object is to provide such an auto air freshener that provides a clip or frame that separates the visual from the fragrance elements in both a decorative and functional manner.

Another object is to provide such an auto air freshener that allows for renewal and updating of its fragrance emitting blotter card and its visual facer card.

Another object is to provide such an auto air freshener that heightens consumer convenience.

Another object is to provide such an auto air freshener that allows for consumers to collect the facer cards.

And, another object is to provide such an auto air freshener that allows for printed advertising upon the facer cards.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In referring to the drawings,

FIG. 3 provides a side view of the invention;

FIG. 4 describes a front view of the clip for the present invention;

FIG. 5 shows an alternate embodiment with a pedestal mount for the present invention;

The same reference numerals refer to the same parts throughout the various figures.

DESCRIPTION OF THE PREFERRED EMBODIMENT

Figure 1:
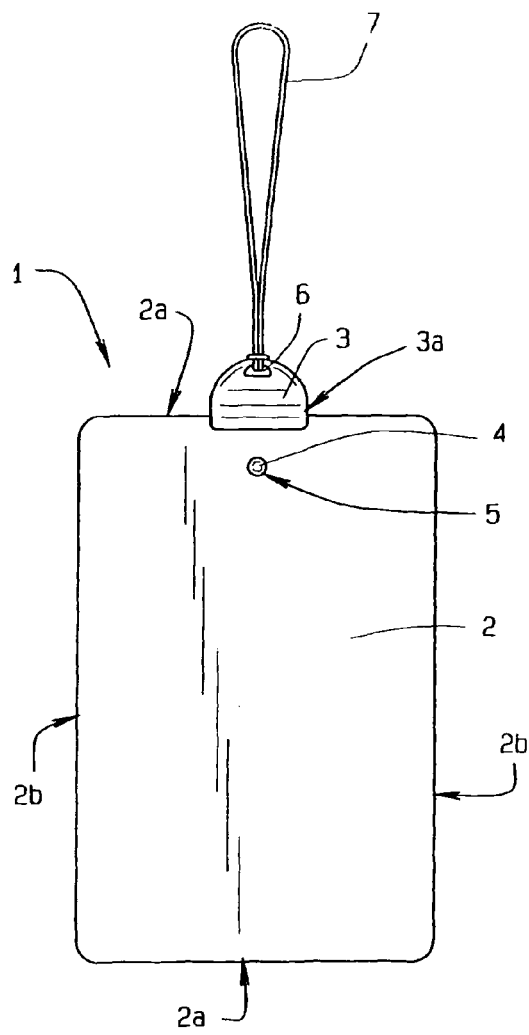
FIG. 1 shows a rear view of the present invention, particularly the air freshening card.
Figure 2:
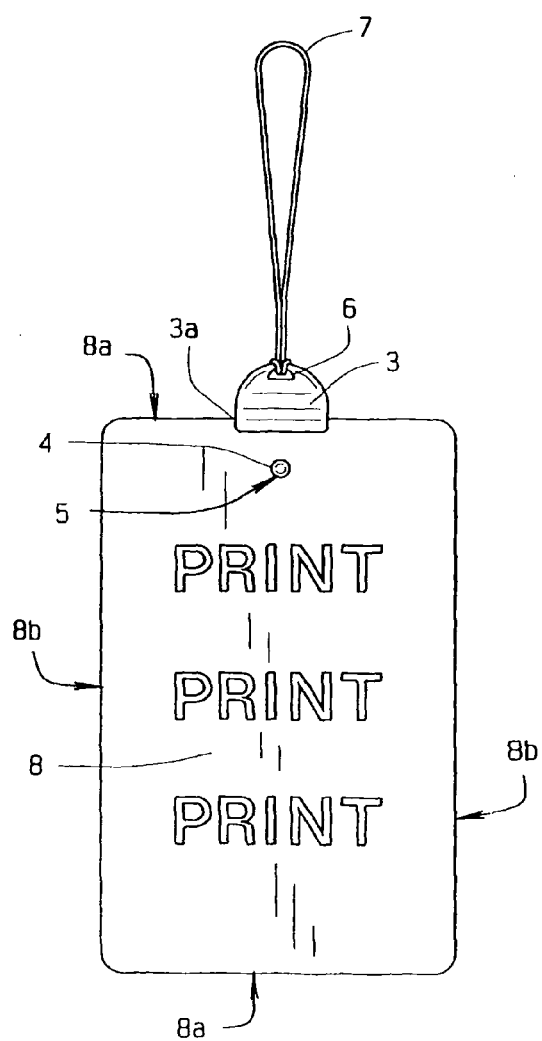
FIG. 2 describes a front view of the present invention, particularly the printed card.

The present art overcomes the prior art limitations by providing an auto air freshener 1 in FIG. 1 that has a blotter board, or an air freshening card 2 having a scent, fragrance, or freshener deposited thereon. The invention can be located in a user's auto, car, truck, home, or office as desired. Behind the air freshening card is a printed card, see FIG. 2. The air freshening card has a generally rectangular shape with two lateral ends 2a and two longitudinal sides 2b, with the lateral ends perpendicular to the longitudinal sides. In the preferred embodiment, the rectangular shape of the air freshening card and the printed card is approximately 2.125 inches by 3.375 inches. Though the previous dimensions are preferred, the applicant foresees air freshening cards and printed cards of other dimensions. In general usage, the longitudinal sides have an upright orientation for the user. Though a rectangular shape is shown, other shapes of the invention are foreseen. The other shapes include polygons, triangular, curved, and round. In this embodiment, the air freshening card secures to a connector, or clip 3, upon a lateral end 2a. The clip receives the air freshening card in mechanical securement that allows for ready installation and replacement of the air freshening card by the manufacturer and later the user. The clip includes a pin 4 that extends into a corresponding punch 5 in the air freshening card. The pin is generally spaced away from the main portion of the clip. The main portion of the clip includes a recess 3a, not shown, that receives the edge of the air freshening card and later the printed card. Opposite the pin, the clip has an aperture 6 that extends through the thickness of the clip. The aperture receives a loop 7, chain, string, line, or other suspension device. Turning the invention as in FIG. 2 reveals a facer card, or a printed card 8, generally of similar shape to the air freshening card as described above. The printed card includes various graphics, text, logos, pictures, or other personalized images. The personalized images include those produced by consumer driven photography websites such as Shutterfly®, Snapfish®, and others. In the preferred embodiment, the printed card has a generally rectangular shape with two lateral ends 8a and two longitudinal side's 8b perpendicular to the lateral ends. The printed card connects to the clip 3 upon a lateral end 8a in mechanical securement that allows for ready installation and replacement of the printed card by the manufacturer and later the user. The clip has its pin 4 that extends into a corresponding punch 5 in the printed card and a recess 3a on the clip, not shown, receives the edge of the printed card. The clip generally maintains the air freshening card 2 and the printed card 8 mutually parallel as later shown.

A side view of the present invention is shown in FIG. 3 where the freshening card is spaced apart and parallel to the printed card. Here, the freshening card 2 is to the left and shows a longitudinal side 2b and the printed card 8 is to the right while showing its longitudinal side 8b. This view shows the clip 3 and its connection to the cards. A loop 7 ties to the clip 3 through the aperture 6 as shown in previous figures. The clip has a thickness in this figure through which passes the loop 7. Opposite the aperture, the clip has a stem 9 extending downwardly from the main portion of the clip. The stem has a thickness less than that of the clip and is generally centered upon the thickness of the clip. Generally centered upon the stem, two pins 4 extend outwardly from the stem in opposite directions where one pin engages a punch 5 on the air freshening card 2 and the other pin engages the punch of the printed card 8. The stem extends away from the main portion of the clip for at least the distance between the aperture and the bottom of the main portion of the clip. The pins engage punches in the cards a distance from the lateral edge of the cards thus preventing tearing out of the pins from the cards.

FIG. 4 then shows the clip 3 alone in greater detail. The clip has a main portion 10 generally having a curved top 11 that is proximate the aperture 6 to which connects the loop 7. Below the curved top, the main portion transitions to a generally rectangular shape with a shoulder 12 opposite the curved top. The shoulder extends across the width of the clip and has the recess 3a locating inwardly from the surface of the shoulder. Beneath the shoulder, the clip has a joint 13 from which extends the stem 9. In this embodiment, the joint is shown linear and perpendicular to the perimeter of the clip. The joint, particularly the recess, has a shape similar to that of the perimeter of the air freshening card and the printed card. For rounded cards, the joint can have a curved shape that matches the perimeter of the rounded card. As before in FIG. 3, the stem extends from the clip and opposite from the aperture and has a width similar to that of the main portion 10 of the clip. Opposite the joint, the clip has a lower edge 13a generally rounded into the stem. Approximately halfway between the joint and the lower edge, the stem has the pin 4 extending perpendicular to the plane of the stem. The pin has a generally cylindrical form with a round cross section and a height inside of the thickness of the main portion 10 as shown in FIG. 3 previously. The pin cooperates with a punch in a card of similar shape and diameter.

An alternate embodiment of the invention is shown in FIG. 5 where the freshening card and the printed card are supported upright rather than hung from above as in the preferred embodiment. The alternate embodiment has a base 14, generally round, with a convex cross section rising towards the center of the base. Above the base, a vertical member, such as a pedestal 15, has a slender elongated shape. The pedestal is approximately three times longer than the base is wide and has its own width greater than the height of the base. The pedestal has two opposed ends. At one end, the pedestal connects to the base using a foot 16. The foot secures the pedestal in a cantilevered connection to the base. In an alternate embodiment opposite the foot, the pedestal has an adhesive, hook and loop fastener, thermoplastic resin, and the like for temporarily securing the pedestal to another surface such as a dashboard. Opposite the foot, the pedestal joins to a capital 17 at a joint 19. The capital covers the joint of the pedestal and has a pleasing appearance as it will be seen by users. Here, the capital has a rounded shape of lesser radius than the base and a diameter generally that of the width of the pedestal. The capital includes a shoulder 18 below the rounded shape. The shoulder has greater length than the width of the pedestal and extends symmetrically outwardly from the centerline of the pedestal. Here the shoulder has a truncated elliptical shape with squared ends outwardly from the pedestal. Between the two ends of the pedestal, the pedestal has a face 15a shown and a mutually parallel and opposite face 15b, not shown, generally flat and rectangular in shape. Proximate the joint, the face 15a has a pin 4 extending perpendicular therefrom. The opposite face 15b also has a pin 4. The pins as before are generally cylindrical and round in cross section. The pins extend for approximately the thickness of the shoulder.

Figure 6:
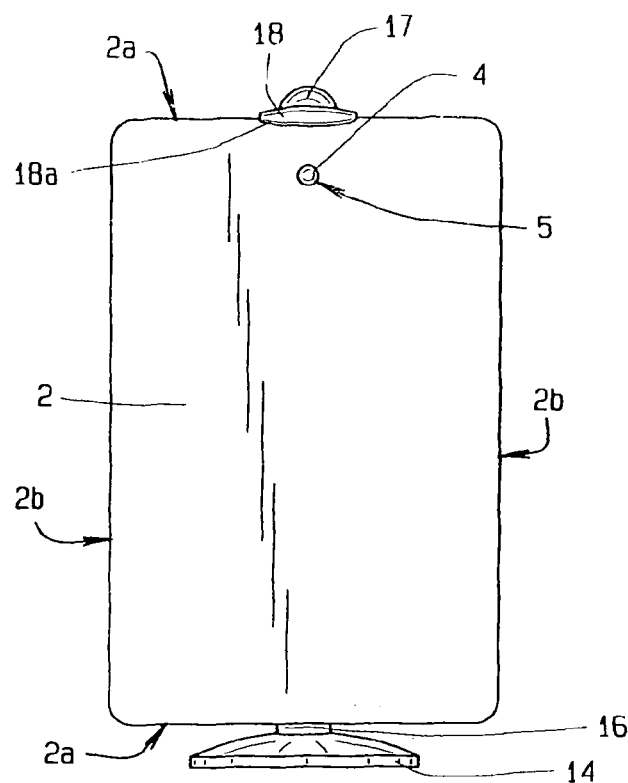
FIG. 6 provides a rear view of an alternate embodiment with an air freshening card.

In usage of the alternate embodiment, FIG. 6 shows an air freshening card 2 positioned upon the pedestal above the base 14. The freshening card has a punch 5 as before that admits the pin 4 through the card. The card then extends beyond the joint 19 into a recess 18a within the shoulder 18, not shown, that receives the edge 2a of the air freshening card. The shoulder generally maintains the air freshening card 2 upright and perpendicular to the base. Though a rectangular air freshening card and substantially straight shoulder are shown, the shoulder may have alternate shapes to correspond to cards having a round or angular shape.

Figure 7:
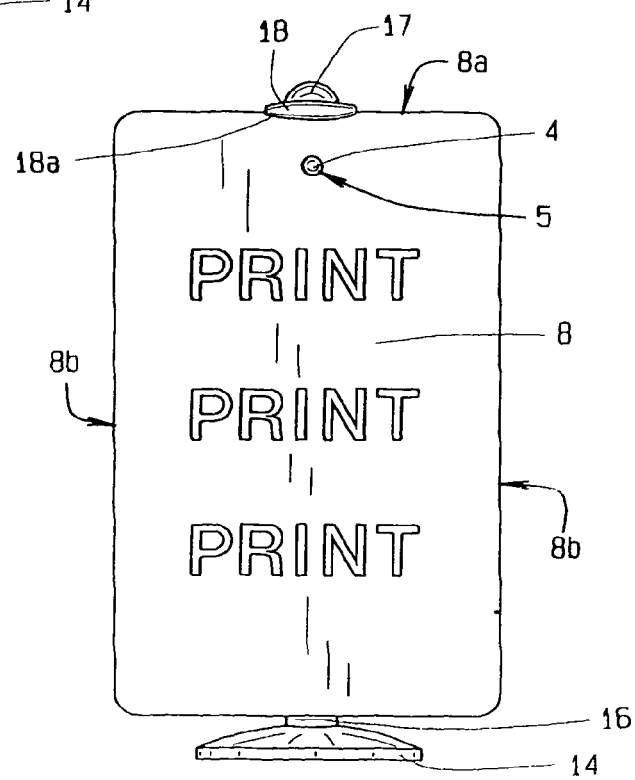
FIG. 7 describes a front view of the alternate embodiment with the printed card.

Then FIG. 7 shows the alternate embodiment in reverse of FIG. 6 with the is printed card 8 showing. The printed card has a punch 5 generally towards one lateral edge 8a that admits a pin 4. The printed card then extends to the shoulder 18 and fits into a recess 18a at the joint. The alternate embodiment provides a scent, fragrance, or freshener and surface for printing that stands by itself at any suitable locating in a home, car, or office. In a further alternate embodiment, a frame replaces the pedestal. The frame has a perimeter of similar shape as the air freshening card and the printed card that allows the invention to blend into a decor.

Figure 8:
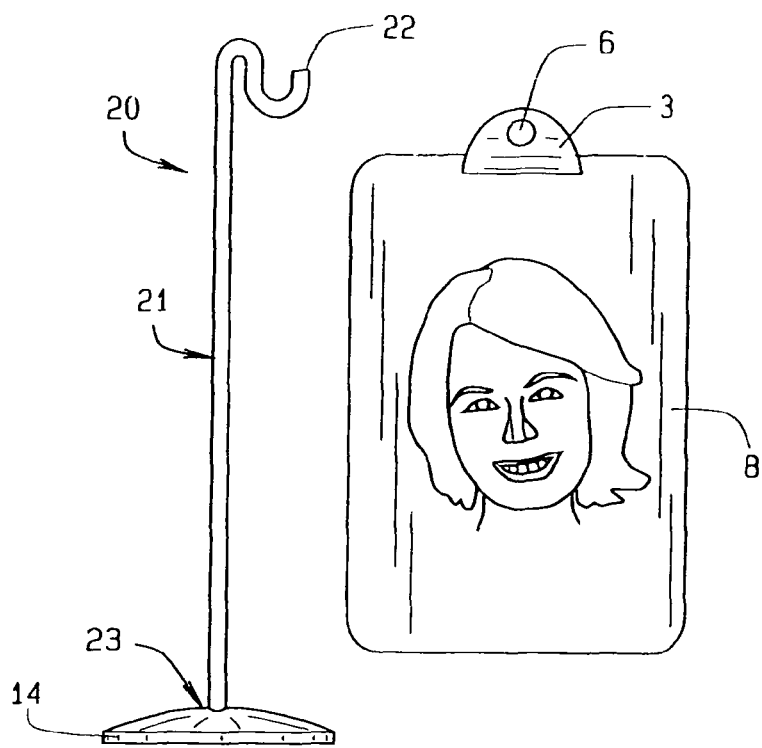
FIG. 8 shows an alternate embodiment suspending the air freshening card and printed card upright; and, FIG. 9A shows a side view of a mechanical clip, and FIG. 9B provides the top view of the mechanical clip; then

FIG. 8 then provides a further alternate embodiment for suspending the air freshening card and the printed card vertically upright. This embodiment has a base 14 as before, generally round, with a convex cross section rising towards the center of the base. Above the base, a wire 20 serves as the vertical member with a rigid, slender elongated shape. The diameter of the wire is a mere fraction of the length of the wire in this embodiment, generally less than 10% of the length. The wire has a length substantially that of the air freshening card and the printed card 8. The wire has sufficient diameter to minimize deflection visible to the user so that the printed card remains at a constant height above the base. The wire has a tip 23 that engages the base and an opposite hook 22. The hook has a substantially S shape that receives the connector 3. Particularly, the aperture 6 of the connector rests upon the hook. The connector then secures the air freshening card and the printed card as previously described with cooperating pins and holes. The printed card has the capability to display printed images, such as photographs. The photographs include personalized images, such as those made by users of Shutterfly®, Snapfish®, and other on demand photo printing services.

Figure 9A:
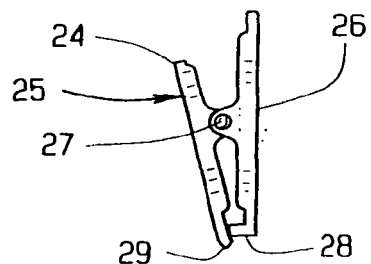
FIG. 9C shows a front view of a slotted clip.
FIG. 9D shows a side view of the slotted clip showing the slots, and both the mechanical clip and the slotted clip grasp the air freshening card and printed card without a hole in the air freshening card and printed card.
Figure 9B:
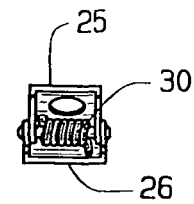

Though connectors with cooperating pins and holes and recesses have been described, the Applicant foresees usage of other connectors with the air freshening card and printed card. Other connectors are shown in FIG. 9 where the connectors grasp the aforementioned card but do not require a die cut hole and a cooperating pin. FIG. 9A shows a side view of a mechanical clip, or a biased hinge clip 24. The clip 24 has a left jaw 25 and an opposite right jaw 26 connected upon a generally centered and transverse pin 27. The pin passes through tabs upon each jaw so that the pin is spaced away from both jaws. The jaws have an inward closed orientation where both jaws have abutting teeth, a tooth 28 on the right jaw and a tooth 29 on the left jaw. The tooth 28 has an overbite of the tooth 29. The overbite strengthens the grip of the teeth upon an object, such as a card, placed with the jaws. Opposite the teeth, each jaw is generally flat and allows for compression by a thumb and forefinger of a user when grasping an object. Viewing the clip away from the teeth in FIG. 9B, the jaws have general U shape construction here with the right jaw 26 having an upright U shape and the left jaw 25 having an inverted U shape. The right jaw is slightly wider than the left jaw and extends outwardly upon the pin 27. Coaxial with the pin and within the left jaw 25, a biasing member 30 abuts both of the jaws. The biasing member extends when a user compresses the flat parts of the jaws together and separates the teeth 28, 29 of both jaws when gripping a card. The biasing member then returns to normal length and forces the flat parts of the jaws apart while closing the teeth firmly upon the surface of a card. The left jaw may have an aperture for suspending the clip from the hook 22 in the alternate embodiment or the loop 7 as in the preferred embodiment.

Figure 9C:
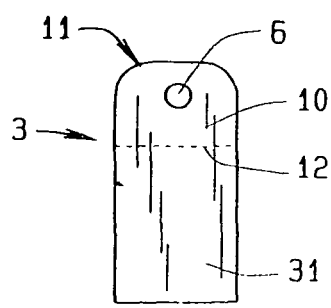
Figure 9D:
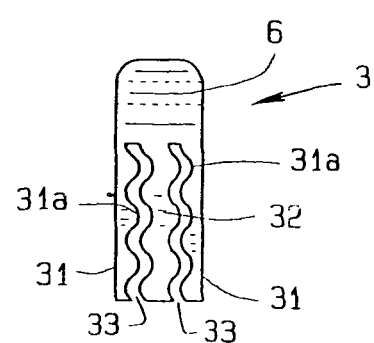

Another connector is shown in FIG. 9C from the front. This connector 3 operates as a pressure grip using friction between itself and the cards, 2, 8. This connector utilizes a main body 10 with a rounded top 11 and an opposite shoulder 12. The main body also has an aperture 6 for admitting a loop, a hook, or other suspension device. Below the shoulder, the connector has an outer finger 31 here shown as generally rectangular with a length slightly more than the radius of the top 11. Turning the connector, FIG. 9D shows a side view that illustrates where cards would insert into the connector. The main body has a thickness, generally at least twice the thickness of an air freshening card or a printed card, and an aperture as described previously. Below the shoulder, the connector has two spaced apart outer fingers 31 that define the front and the back of the connector. Upon the exterior surface, that is visible to the user, the is outer fingers are generally smooth. Upon the interior surface, the outer fingers have a series of spaced apart transverse ridges 31a. Inside of the outer fingers, this connector has at least one inner finger 32. The inner finger has a similar length and width as the outer fingers and two opposing surfaces generally parallel to the front and the back of the connector. The opposing surfaces are spaced apart by a thickness that defines the spacing of the air freshening card 2 from the printed card 8. Opposite the shoulder, the spacing between the inner finger and the outer fingers define slots 33 for receiving the edge of a card. The inner finger though has a series of spaced apart transverse ridges upon both surfaces. The ridges upon the inner finger face the ridges of both outer fingers. The ridges of both the inner finger and the outer fingers cooperate to engage the surface of the air freshening card and the printed card by friction so that both cards remain with the connector but with the use of a hole in the cards. To utilize this embodiment of the connector, a user inserts a lateral edge of a card into one slot and pushes the card towards the shoulder and then inserts a lateral edge of the other card into the other slot and pushes it towards the shoulder. The ridges upon the surfaces of the outer fingers and the inner finger then grip the surfaces of the card so that the cards remain with the connector as a frictional connection overcomes the weight of the cards. The aperture of this embodiment of the connector then provides a place to suspend the connector and cards as previously described.

In a further alternate embodiment, the freshening card 2 and printed card 8 include a debossed indentation. The debossment has a generally linear shape recessed into the surface of the cards. The debossment cooperates with the teeth 28, 29 of the hinge clip 24. The teeth fit within the debossment and the depth of the debossment prevents a card from slipping from the clip by the mechanical action of the teeth against the debossment walls. The debossment though does not penetrate completely through the cards thus obviating the usage of a cutting die.

Then in a further alternate embodiment, the base 14 contains a reservoir of fragrance and has a linear slot generally parallel to the diameter of the base and extending at least partially through the convex cross section. The slot intersects the reservoir at least partially along its length. Then a freshening card 2 has its lateral edge 2a inserted into the slot. The material of the freshening card then draws the fragrance through the card using capillary action similar to a wick. The card then releases the fragrance from the embodiment into the nearby environment.

And in a further alternate embodiment, the connector 3 is generally hollow below the aperture 6. The connector has a reservoir therein for storing liquid fragrance. The reservoir has a small pore opposite the aperture and generally within the recess 3a. The user then inserts the freshening card within the recess as before until the card abuts the connector. When the card abuts the pore, capillary action, such as in a wick and gravity slowly disperse the fragrance through the pore into the material of the freshening card. The freshening card then distributes the fragrance into the environment around the embodiment. In this alternate embodiment, the connector and the freshening card are generally suspended vertically.

From the aforementioned description, an auto air freshener has been described. The device is uniquely capable of providing a fragrance or scent from a freshening card mutually parallel to and spaced apart from a printed card connected by a clip or pedestal mount. The air freshening card has a fragrance or scent deposited thereon and the printed card has various indicia, lettering, or images placed thereon using existing printing techniques. The auto air freshener and its various components may be manufactured from many materials, including but not limited to, cardstock, papers, polymers, ferrous and non-ferrous metals, their alloys, and composites, and the fragrance or scent may include various ingredients as is known in the fragrance art.

As such, those skilled in the art will appreciate that the conception, upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

We claim:

1. A device for dispensing a freshening scent simultaneously with displaying a visual image, comprising:
    an air freshening card having an edge around its perimeter and including an upper edge;
    at least one printed card, having an edge around its perimeter and including an upper edge, said printed card being of the same size as said freshener card and being arranged parallel to said air freshener card;
    a connector supporting said air freshener card and said printed card at their upper edges in a spaced apart relationship and generally vertically, said connector including a clip portion, a stem integrally extending from said clip portion, said stem being recessed inwardly from both sides of the clip portion, and said air freshener card and said printed card being pinned to opposite sides of the recessed stem of the connector; and
    wherein one of said air freshener card and said printed card faces a user of the device during application.

2. The dispensing device of claim 1 wherein said air freshening card is approximately two inches wide and approximately three inches long and said at least one printed card is approximately two inches wide and approximately three inches long.

3. The dispensing device of claim 1 wherein said air freshening card and said printed card each has a rectangular shape.

4. The dispensing device of claim 1 further comprising:
    said printed card having at least one personalized image thereon.

* * * * *